(12) United States Patent  
Mehendale et al.

(10) Patent No.: US 7,903,238 B2  
(45) Date of Patent: Mar. 8, 2011

(54) COMBINATION OF ELLIPSOMETRY AND OPTICAL STRESS GENERATION AND DETECTION

(75) Inventors: Manjusha Mehendale, Princeton, NJ (US); Michael J. Kotelyanskii, Chatham, NJ (US); Yanwen Hou, Hackettstown, NJ (US); Jim Onderko, Gibsonia, PA (US); Guray Tas, Flanders, NJ (US)

(73) Assignee: Rudolph Technologies, Inc., Flanders, NJ (US)

( * ) Notice: Subject to any disclaimer, the term of this patent is extended or adjusted under 35 U.S.C. 154(b) by 0 days.

(21) Appl. No.: 12/309,166

(22) PCT Filed: Jul. 9, 2007

(86) PCT No.: PCT/US2007/015286  
§ 371 (c)(1),  
(2), (4) Date: Jan. 9, 2009

(87) PCT Pub. No.: WO2008/008223  
PCT Pub. Date: Jan. 7, 2008

(65) Prior Publication Data  
US 2009/0244516 A1 Oct. 1, 2009

(51) Int. Cl.  
*G01B 11/16* (2006.01)  
*G01J 4/00* (2006.01)  
(52) U.S. Cl. ........................................... 356/33; 356/369  
(58) Field of Classification Search ................ 356/33, 356/369  
See application file for complete search history.

(56) References Cited

U.S. PATENT DOCUMENTS

| | | | |
|---|---|---|---|
| 5,748,318 A | 5/1998 | Maris et al. | 356/381 |
| 5,973,787 A | 10/1999 | Aspnes et al. | 356/369 |
| 6,068,539 A * | 5/2000 | Bajaj et al. | 451/6 |
| 6,069,703 A | 5/2000 | Banet et al. | 356/432 |
| 6,321,601 B1 | 11/2001 | Maris | 73/657 |
| 2001/0028460 A1 | 10/2001 | Maris et al. | 356/432 |
| 2003/0076497 A1 | 4/2003 | Wolf et al. | 356/369 |
| 2007/0097370 A1 | 5/2007 | Chism | 356/432 |

OTHER PUBLICATIONS

A. Moritani, Y. Okada, and J. Nakai, "Use of an ADP four-crystal electrooptic modulator in ellipsometry", Applied Optics, vol. 22, (1983), pp. 1329-1337.  
A. Moritanti, Y. Okada, H. Kubo, and J. Nakai, "High-speed retardation modulation ellipsometer", Applied Optics, vol. 22, (1983), pp. 2429-2436.  
Robert F. Enscoe and Richard J. Kocka, "Systems and Applications Demands for Wider-Band Beam Modulation Challenge System Designers", copyright 1981-2005 by Conoptics Inc.

* cited by examiner

*Primary Examiner* — Roy Punnoose  
(74) *Attorney, Agent, or Firm* — Harrington & Smith

(57) ABSTRACT

A method includes selecting one of performing ellipsometry or performing optical stress generation and detection. The method also includes, in response to selecting performing ellipsometry, applying at least one first control signal to a controllable retarder that modifies at least polarization of a light beam, and performing ellipsometry using the modified light beam. The method further includes, in response to selecting performing optical stress generation and detection, applying at least one second control signal to the controllable retarder, and performing optical stress generation and detection using the modified light beam. Apparatus and computer readable media are also disclosed.

24 Claims, 12 Drawing Sheets

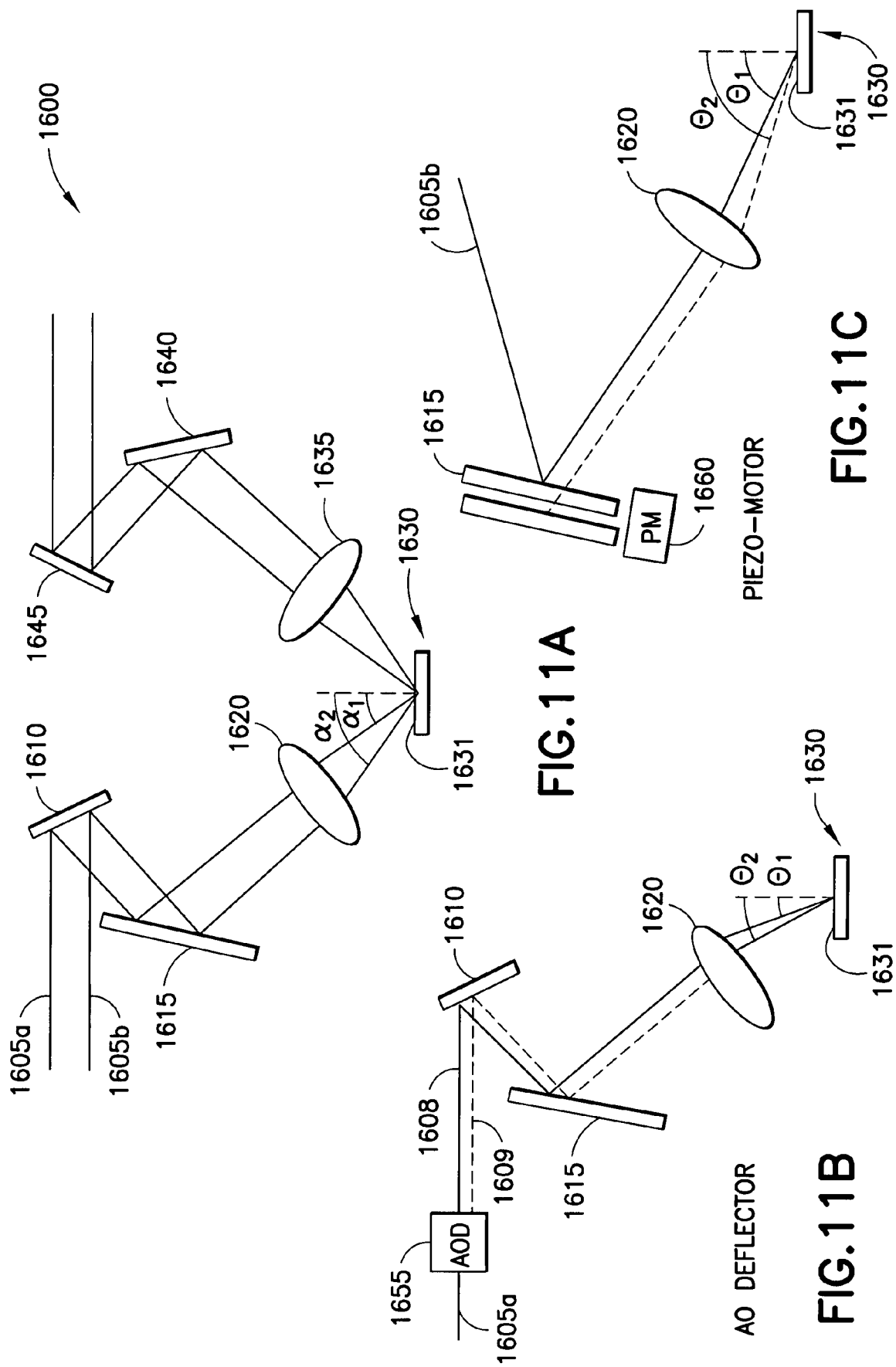

COMBINATION OF ELLIPSOMETRY AND OPTICAL STRESS GENERATION AND DETECTION

TECHNICAL FIELD

This invention relates generally to measuring characteristics of samples and, more specifically, relates to ellipsometry and optical stress generation and detection.

BACKGROUND

There are many different techniques for measuring characteristics of samples such as, for example, semiconductors. One such technique is ellipsometry, in which the polarization change of a light beam is measured when the light beam is reflected by the sample. This change in polarization is then related to characteristics of the sample. Ellipsometry is generally used for transparent materials, but may also be used for very thin, opaque films.

Another technique is optical stress generation and detection. This technique is described, e.g., in Maris et al., "Optical Stress Generator and Detector", U.S. Pat. No. 5,748,318, May 5, 1998, and Humphrey Maris, "Optical Method for the Characterization of Laterally-Patterned Samples in Integrated Circuits", U.S. Pat. No. 6,321,601, Nov. 27, 2001. These references contain detailed information about optical stress generation and detection for characterization of samples and should be consulted for their disclosure of optical stress generation and detection. Briefly, in optical stress generation and detection, a "pump" beam is used to perturb the sample, and a "probe" beam is used to analyze results of the perturbation. For instance, the pump beam could generate a stress wave that causes properties of a layer on the sample to change, and the probe beam is used to analyze the property changes. The resultant property changes are then used to determine characteristics of, e.g., the layer. Optical stress generation and detection may be used on opaque materials.

While both ellipsometry and optical stress generation and detection are useful analysis techniques, systems using these techniques could be improved.

BRIEF SUMMARY

In an exemplary embodiment, a method is disclosed that includes selecting one of performing ellipsometry or performing optical stress generation and detection. In response to selecting performing ellipsometry, at least one first control signal is applied to a controllable retarder that modifies at least polarization of a light beam directed to a surface of a sample, and ellipsometry is performed using a version of the modified light beam reflected from the sample in order to determine at least one first characteristic of the sample. In response to selecting performing optical stress generation and detection, at least one second control signal is applied to the controllable retarder, and optical stress generation and detection is performed using the reflected version of the modified light beam in order to determine at least one second characteristic of the sample.

In another exemplary embodiment, an apparatus has at least a first configuration used to perform ellipsometry and a second configuration used to perform optical stress generation and detection. The apparatus includes a pump beam and a probe beam, each of the beams directed to a surface of a sample. A controllable retarder is placed in a path of a selected one of the pump beam or the probe beam. The controllable retarder is configured to modify at least polarization of the selected beam. A controller is coupled to the controllable retarder and is configured to provide at least one control signal to the controllable retarder. The controller is configured in the first configuration to cause at least one first control signal to be applied to the controllable retarder. The controller is configured in the second configuration to cause at least one second control signal to be applied to the controllable retarder, wherein the at least one first control signal and the at least one second control signal cause different polarizations of the selected beam. The apparatus also includes a detector configured to receive a version of the selected beam reflected from the surface of the sample and to output data corresponding to the reflected version. The apparatus further includes a data analysis module coupled to the detector and configured in the first configuration to perform data analysis using the output data in order to determine at least one first characteristic of the sample, and further configured in the second configuration to perform data analysis using the output data in order to determine at least one second characteristic of the sample.

In a further exemplary embodiment, a computer-readable medium is disclosed having a program of computer-readable instructions tangibly embodied thereon, the instructions executable by a processing unit to perform operations. The operations include selecting one of performing ellipsometry or performing optical stress generation and detection. In response to selecting performing ellipsometry, at least one first control signal is applied to a controllable retarder that modifies at least polarization of a light beam directed to a surface of a sample, and ellipsometry is performed using a version of the modified light beam reflected from the sample in order to determine at least one first characteristic of the sample. In response to selecting performing optical stress generation and detection, at least one second control signal is applied to the controllable retarder, and optical stress generation and detection is performed using the reflected version of the modified light beam in order to determine at least one second characteristic of the sample.

BRIEF DESCRIPTION OF THE DRAWINGS

The foregoing and other aspects of embodiments of this invention are made more evident in the following Detailed Description of Exemplary Embodiments, when read in conjunction with the attached Drawing Figures, wherein:

FIG. 11A is a diagram of a system used to direct a light beam onto a sample at a number of angles of incidence;

FIGS. 11B and 11C are other diagrams of systems for providing a number of angles of incidence of the pump or probe beam;

DETAILED DESCRIPTION OF EXEMPLARY EMBODIMENTS

As described above, both ellipsometry and optical stress generation and detection are useful analysis techniques. Each technique has certain benefits and detriments. In general, ellipsometry is not functional on opaque layers. However, ellipsometry may be used on opaque materials where the layers are very thin, e.g., 50 (Å) or less. Optical stress generation and detection has the capability of measuring opaque layers down to about 50 angstroms (Å), while ellipsometry will measure layer thicknesses of about 10 Å and less. Therefore, a user may desire to use both ellipsometry and optical stress generation and detection in order to perform, e.g., measurements on a wide range of film thicknesses. For instance, a semiconductor wafer holding a number of integrated circuits may have a number of devices and layers, each of which has certain thicknesses. Thus, on the same wafer, multiple thickness layers could be tested. Electro-optic modulators (EOMs) have also been used for ellipsometry. See, e.g., Applied Optics, vol. 22, pages 1329 and 2429 (1983).

However, there is a problem in that a system for performing ellipsometry and a system for optical stress generation and detection are typically separate systems. Therefore, it would be beneficial to provide a single system that can be configured to perform both ellipsometry and optical stress generation and detection.

Aspects of the disclosed invention disclose systems, methods, and computer-readable medium for combination ellipsometry and optical stress generation and detection. Accordingly, combining the two measurement techniques into a single metrology tool allows, e.g., for the measurement of both transparent and opaque materials having a variety of thicknesses from above 50 Å down to a thickness of, e.g., around 10 Å. Such a tool would also allow testing of multiple locations, with possibly multiple characteristics, on a single wafer.

Figure 1:
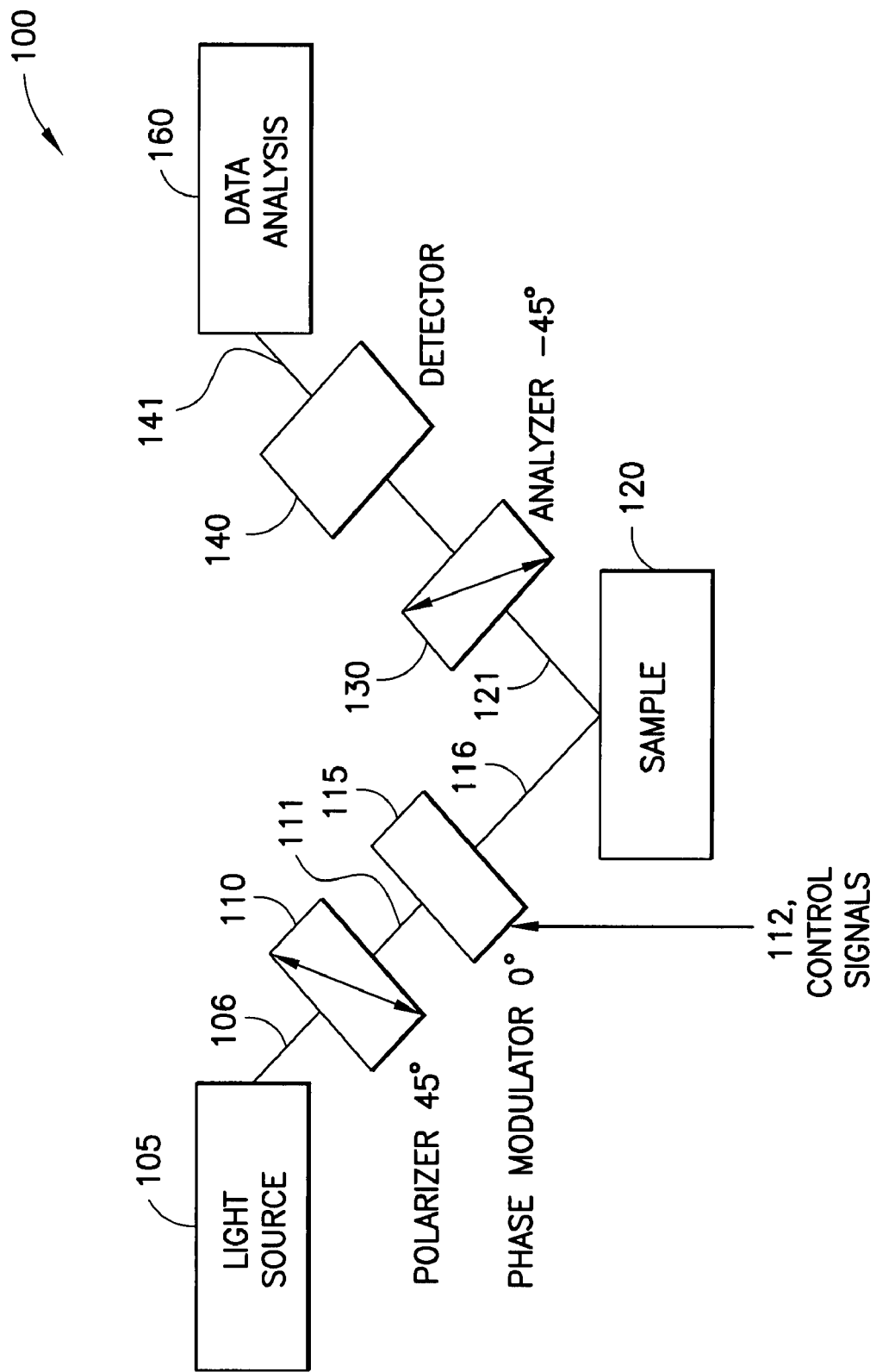
FIG. 1 is a block diagram of a system suitable for performing ellipsometry.

Turning now to FIG. 1, a block diagram is shown of a system 100 suitable for performing ellipsometry. FIG. 1 is used to present a system suitable for performing ellipsometry and to discuss problems introduced when attempting to perform measurements with both an ellipsometry system and an optical stress generation and detection system. This ellipsometry system 100 includes a light source 105, such as a laser, that directs light beam 106 through a polarizer 110 (having, for example, a phase of 45 degrees), which creates a polarized beam 111, and through a phase modulator 115 (having an initial phase of zero degrees), which creates a phase modulated beam 116, onto a sample 120. Phase modulator 115 may be an electro-optical modulator (EOM), a photoelastic modulator (PEM), an LCD (liquid crystal display) based phase modulator, any other type of controllable retarder, or an equivalent thereof. The light beam 116 reflects off the sample as reflected beam 121 and travels through an analyzer 130 (having a phase of −45 degrees) to a detector 140. The detector 140 produces one or more signals 141 that are analyzed by a data analysis module 160. Such data analysis could further include amplification of the signal(s) 141, analog-to-digital conversion of the signals 141, and several different analyses to determine characteristics of the sample 120 known to those skilled in the art. A modulation is applied to the phase modulator 115 using the one or more control signals 112 at the modulation frequency of "f".

Figure 3:
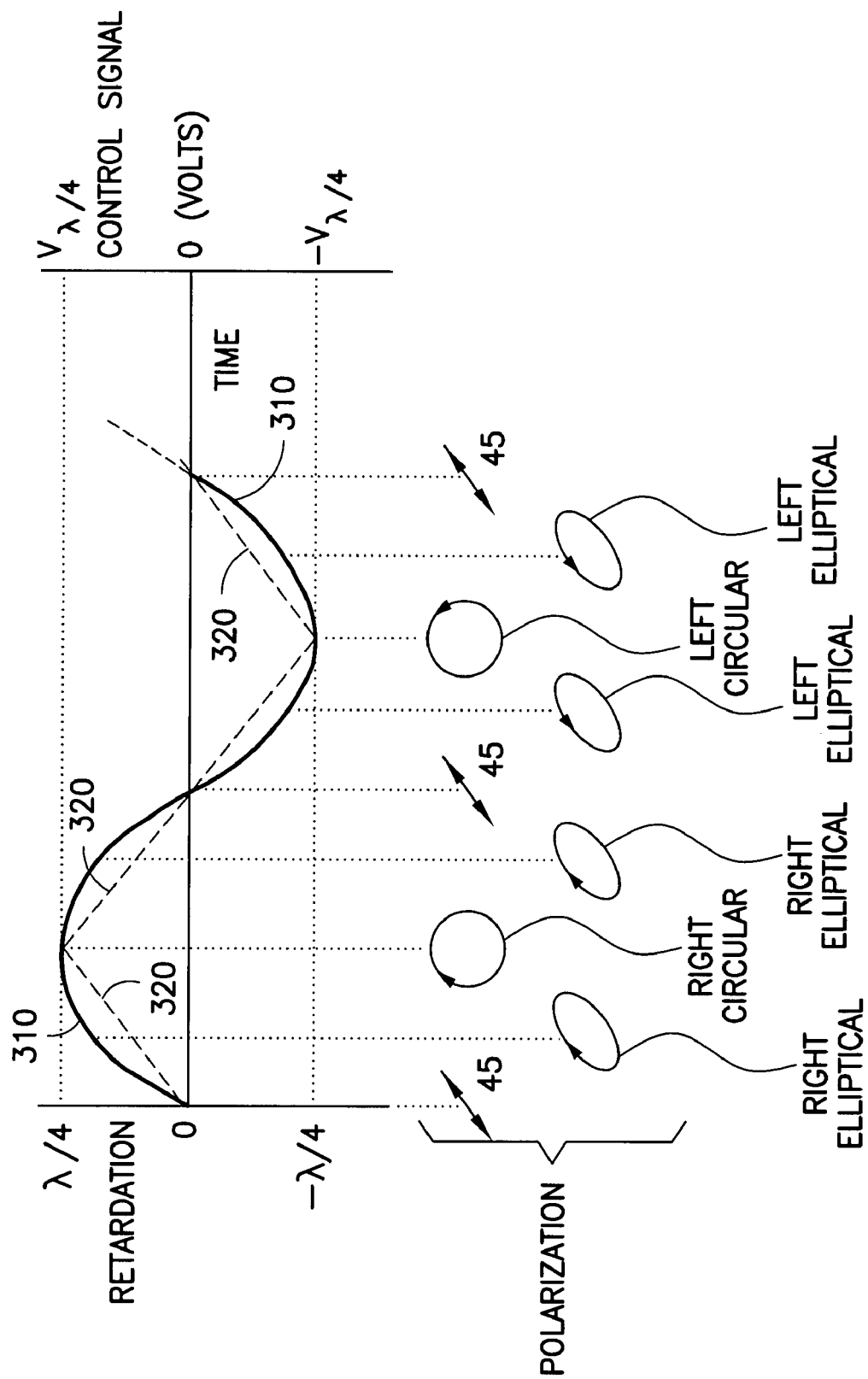
FIG. 3 is an exemplary graph of retardation applied by an electro-optic modulator (EOM) in FIG. 2 and resultant polarization occurring in a phase modulated beam of FIG. 2.

The phase modulator 115 provides phase modulation, which means that linearly polarized light 111 (i.e., from the polarizer 110) is phase modulated by the phase modulator to have a periodicity (as determined by the modulation frequency, f) in the light beam 116. This modulation modifies one of the p and s components of the polarization relative to the other component. Therefore, the phase between the p and s components of the polarization is also modified. As shown in FIG. 3 below, the periodicity modifies the polarization of the light beam 116 to oscillate between linear polarization and circular polarization. Circular polarization is useful for ellipsometry, as the sample 120 modifies the polarization from circular polarization in the incident light beam 116 to, e.g., ellipsoidal polarization in the reflected light beam 121.

The resultant signal 141, which contains information concerning the ellipsometric polarization of the reflected light beam 121, is demodulated, by way of example only, using lock-in detection techniques, or using digital signal processing applying Fourier transforms or convolution with other suitable basis functions, depending on the phase modulation function applied, using control signal(s) 112, to the modulator 115. These techniques give the ellipsometric parameters Ψ and Δ. As is known, the ellipsometric parameter Ψ is related to the magnitude, r, of the p and s components of the polarization:

$$\tan(\Psi) = \frac{r_p}{r_s}.$$

The ellipsometric parameter Δ is related to the phase, ϕ, between the p and s components of the polarization: $\Delta = \phi_p - \phi_s$. Thus, the modification by the sample 120 of the polarization from circular polarization in the incident light beam 116 to ellipsoidal polarization in the reflected light beam 121 provides the ellipsometric parameters Ψ and Δ.

In contrast to conventional null-ellipsometry, phase modulation ellipsometry as described above can achieve higher sensitivity and lower noise. Furthermore, phase modulation ellipsometry eliminates the need for a rotating compensator, thus increasing the response time considerably and making the setup less susceptible to vibrations and optical misalignment. Reproducibility of modulation amplitude also eliminates frequent recalibration.

As explained above in reference to FIG. 1 and in more detail in reference to FIG. 3, systems that perform phase modulation ellipsometry use phase modulation to create a known, periodic polarization of the incident light beam 116.

Furthermore, these systems do not modify the amplitude of the incident light beam 116 in any significant manner. By contrast, as explained in more detail in reference to FIGS. 4 and 5, a system using optical stress generation and detection is concerned mainly with modification of the amplitude of the incident light beam 116. Because a phase modulation ellipsometry system and an optical stress generation and detection system use different techniques in preparing incident light beam 116 for use with each respective technique, typically two separate systems are used for these techniques. An aspect of the disclosed invention relates to systems that can be configured to perform both techniques.

Figure 2:
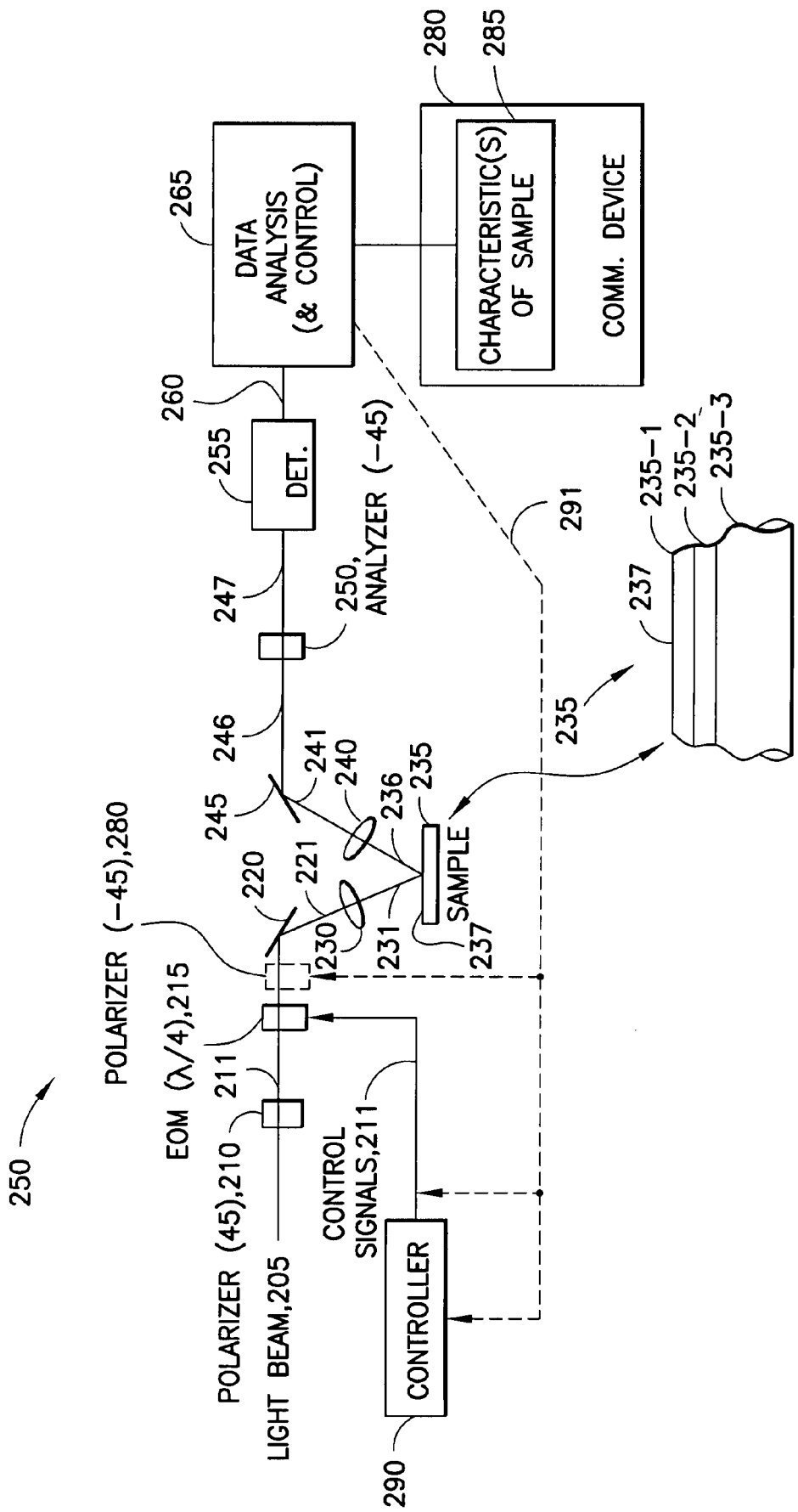
FIG. 2 is a block diagram of an exemplary system for performing both ellipsometry and optical stress generation and detection when the system is configured to perform ellipsometry.
Figure 4:
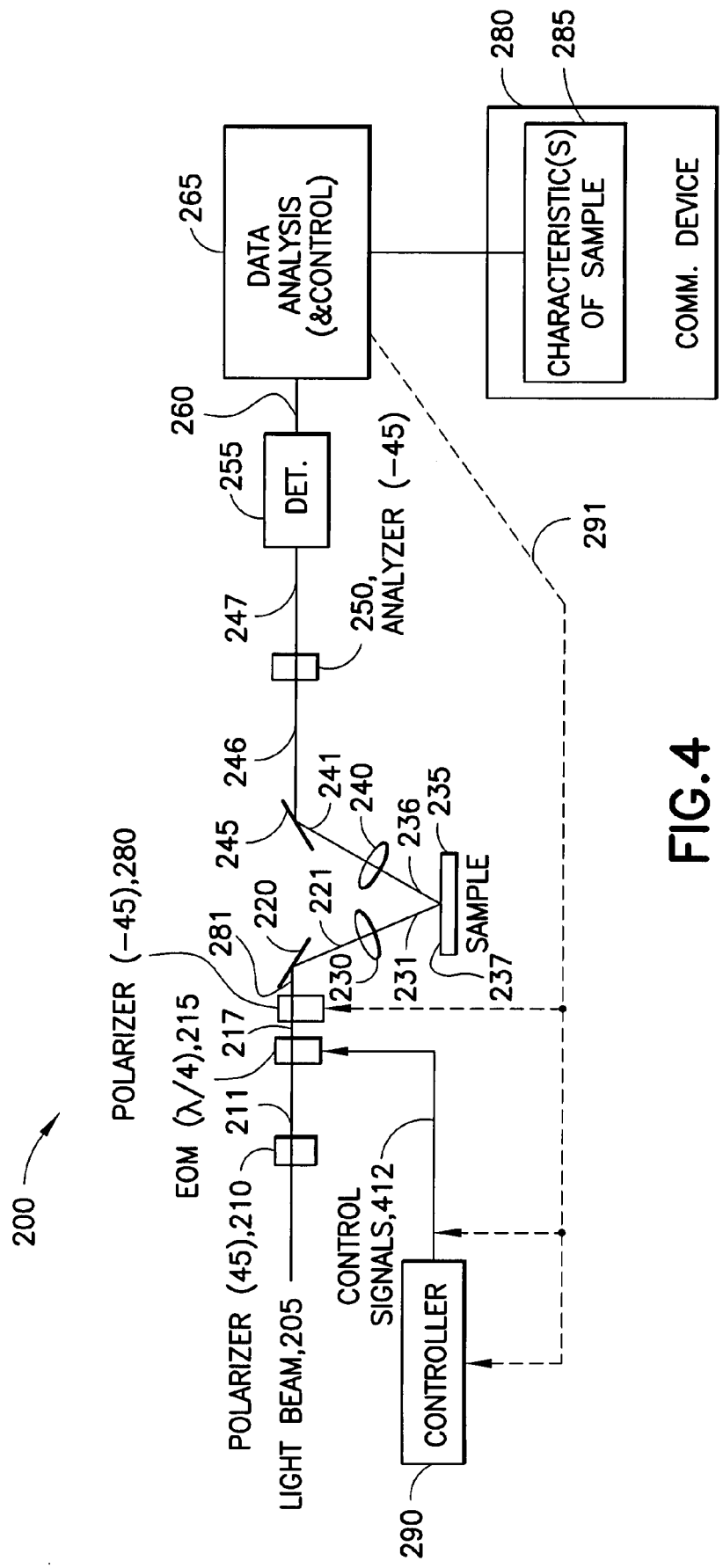
FIG. 4 is a block diagram of the system shown in FIG. 2 when the system is configured to perform a portion of optical stress generation and detection.
Figure 5:
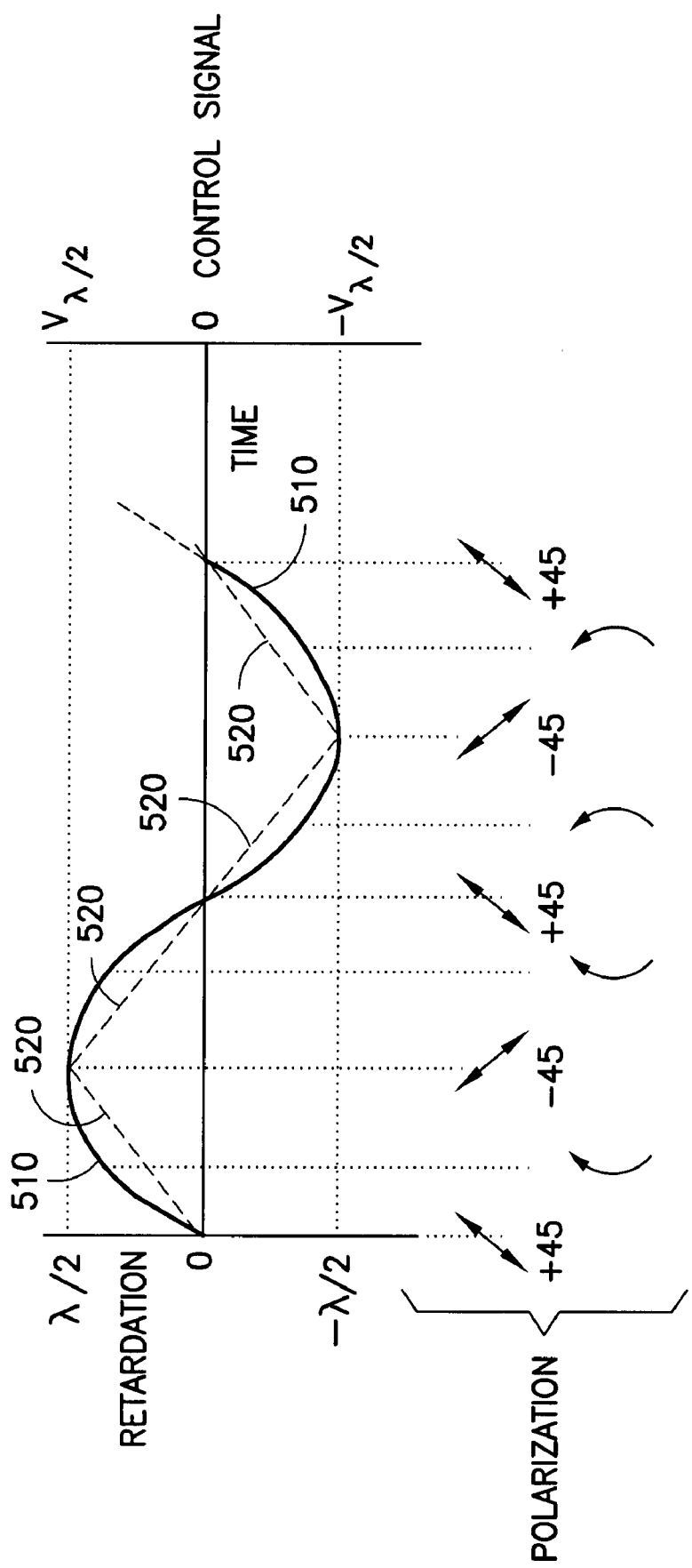
FIG. 5 is an exemplary graph of retardation applied by the EOM in FIG. 4 and resultant polarization occurring in a modulated beam of FIG. 4.

Now that an introduction has been made to ellipsometry and problems with use of separate systems to perform ellipsometry and optical stress generation and detection, a description will now be given of an exemplary system useful for performing both ellipsometry and optical stress generation and detection. Additionally, a further analysis will be given as to why ellipsometry systems are typically separate from optical stress generation and detection systems. FIGS. 2 and 3 are directed to use of a controllable retarder, such as an EOM, in a system to perform ellipsometry, and FIGS. 4 and 5 are directed to use of the controllable retarder in the same system to perform optical stress generation and detection.

Turning to FIG. 2, an exemplary system 200 is shown for performing ellipsometry that may be readily adapted for optical stress generation and detection. System 200 comprises a polarizer 210, a controllable retarder 215, a mirror 220, a lens 230, a lens 240, a mirror 245, an analyzer 250, a detector 255, a controller 290, a data analysis and control module 265, and a communication device 280. A light beam 205, generated by a laser (not shown in FIG. 2 or 4) for instance, proceeds through the polarizer 210, which creates a polarized beam 211. The controllable retarder 215 (in this embodiment, an EOM) modifies the polarized light beam 211 to create a phase modulated beam 216. The phase modulated beam 216 is directed by the mirror 220 onto the lens 230, which focuses the phase modulated beam 215 onto the sample 235 as focused beam 231. A reflected beam 236 is reflected off the sample 235 and is directed through the lens 240, which creates a collimated beam 241. Collimated beam 241 is directed by mirror 245, as beam 246, to the analyzer 250. Analyzer 250 produces a resultant beam 247, which is examined by the detector 255. Detector 255 produces detected signal(s) 260, which is analyzed by the data analysis and control module 265. It is noted that the sample 235 may have multiple layers, including layer 235-1 (e.g., a conductive layer), layer 235-2 (e.g., an insulating layer), and layer 235-3 (e.g., a substrate). Characteristics may be determined for one or more of the layers 235-1 through 235-3 and in particular layers 235-1 and 235-2.

The polarizer 280 is shown using a dashed line, because the polarizer 280 is typically not used for ellipsometry. The data analysis and control module 265 produces one or more characteristics 285 of the sample 235. The one or more characteristics 285 may be output using a communication device 280, which could be a hard drive, display, or printer. The one or more characteristics 285 for ellipsometry include, e.g., thickness of one more layers on the sample 235. Other than measuring the thickness of a thin layer, ellipsometry is useful in determining the real and imaginary parts of the dielectric constant of the material (which is how ellipsometry gives a value for thickness in a way). This data can be useful in studying the material properties of the layer. If incorporated with femtosecond pulse ellipsometry, it is possible to study ultrafast carrier dynamics.

It is noted that the controllable retarder 215 is any device that modifies at least polarization of a light beam. The modification of polarization occurs because one of the p and s components of the polarization is modified relative to the other component. Therefore, the phase between the p and s components of the polarization is also modified. Any controllable retarder may be used. It may be possible, for example, to use a phase modulator 115 such as a PEM or an LCD (liquid crystal display) based phase modulator. A PEM operates in a similar way to modify polarization as an EOM. A difference between a PEM and an EOM lies in that PEM only works at a certain resonant frequency, which is typically 50 kHz for fused silica, and a PEM typically cannot be externally triggered. An EOM on the other hand has a large bandwidth, up to a few megahertz (MHz), and can be externally triggered and synchronized with a laser and the rest of the electronics (e.g., detector 255 and data analysis and control module 265), which becomes important for performing both ellipsometry and optical stress generation and detection. In other words, because of the synchronization issue, with PEM it may not be possible to perform both ellipsometry measurements optical stress generation and detection. An EOM facilitates synchronization through changing the bias voltage, though other modifications may also be required in some instances. Also, since an EOM can be modulated at higher frequencies as compared to the PEM, a measurement of either ellipsometry or optical stress generation and detection can be faster.

The controller 290 produces, in an exemplary embodiment, the control signal(s) 211. The controller 290 may be part of the controllable retarder 215. In an exemplary embodiment, the data analysis and control module 265 allows a user (not shown) to select between ellipsometry and optical stress generation and detection and to control the controller 290 to select an appropriate set of control signal(s) (e.g., control signal(s) 211 of FIG. 2 or control signals 411 of FIG. 4) or to send the control signal(s) (e.g., 211 or 411) to the controllable retarder 215. The data analysis and control module can also control the polarizer 280 to move into or out of the path of light beam 211, and to determine appropriate analysis performed to produce the characteristics 285. In another embodiment, the controller 290 is manually programmed with appropriate control signal(s) 211 (or 411; see FIGS. 4 and 5), the polarizer 280 is manually placed into or out of the path of light beam 211, and the appropriate analysis is performed based on user control over performing an appropriate data analysis based on which of ellipsometry or optical stress generation and detection is performed. Thus, the systems described herein can include a range of user interaction, from a large amount of user interaction to no user action (e.g., the systems are fully automated).

In the system shown in FIG. 2, in an exemplary embodiment, the EOM 215 is switched off and the analyzer 250 is adjusted for minimum light through the analyzer 250. The EOM 215 is switched on and a sinusoidal bias voltage (e.g., as applied by one or more control signals 212) is adjusted so that the EOM 215 acts as a quarter-wave plate with a certain period. Such an observation may be made, for instance, using an oscilloscope. In the example of FIG. 2, the sinusoidal driving voltage is applied to the electro-optic modulator prior to making the observation of the sinusoidal signal on the oscilloscope, and then the bias voltage is adjusted so that the EOM 215 acts as a quarter-wave plate. The control signal(s) 212 to the electro-optic modulator is therefore a bias voltage that causes a periodic quarter-wave operation of the electro-optic modulator.

When performing the ellipsometry measurements, a relatively large trace (e.g., several cycles, where one cycle is shown in FIG. 3) out of the analyzer 250 is examined using the detector 255. The signal(s) 260 from the detector 255 is sent to the data analysis and control module 265, such as one or more lock-in-amplifiers or an oscilloscope with suitable bandwidth (e.g., sampling frequency), or a digital signal processor. The digital signal processor performs fast Fourier transform (FFT) on a resultant trace from the signal(s) 260. A lock in amplifier has band-pass filters that block most of the frequencies except the frequencies being examined. Data is collected at different harmonics of the modulation frequency, which is set at, e.g., 500 kHz. Typically, DC (direct current), 1f, and 2f frequencies are examined. In the case of a digital signal processor, the whole trace, which has about, e.g., 20 cycles for efficient FFT, is saved. Analysis may also be performed using, e.g., digital signal processing at a computer, and the digital signal processing gives various harmonics of the modulation frequency.

FIG. 3 is an exemplary graph of retardation applied by the EOM 215 in FIG. 2 and resultant polarization occurring in the phase modulated beam 216. The retardation applied by the EOM 215 is shown as a sinusoidal signal 310 and indicates a retardation in polarization from "zero" to quarter-wave ($\lambda/4$) retardation (e.g., the EOM 215 acts as a quarter-wave plate). The retardation portion of FIG. 3 shows a sinusoidal control signal 212 (e.g., as voltage) that is applied to the EOM 215 to create the corresponding retardation waveform. The sinusoidal control signal 212 is sinusoidally varied between $$V_{\lambda/4} \text{ and } -V_{\lambda/4}.$$

When the retardation is zero, the polarization is +45 (e.g., the polarization of the polarized beam 211). When the retardation is $\lambda/4$, the polarization is right circular. When the retardation is $-\lambda/4$, the polarization is left circular. The retardation modulation amplitude may be higher, or lower, than $\lambda/4$, and such lower or higher amplitude has to be accounted for in further processing the measured signal to extract ellipsometric parameters $\Psi$ and $\Delta$.

It is noted that sinusoidal signal 310 is merely one example of a retardation modulation signal. Sawtooth signal 320 may also be used, as could a number of other signals.

Referring now to FIGS. 4 and 5, FIG. 4 shows a block diagram of the system 200 shown in FIG. 2 when the system is configured to perform a portion of optical stress generation and detection. The light beam 205 in the example of FIG. 4 is one of the pump beam or the probe beam for the optical stress generation and detection analysis. In the example of FIG. 4, one or more control signals 412 are modified to operate the EOM 215 as a periodic half-wave plate to create the phase modulated beam 217. A second polarizer 280 is placed after the EOM 215 and operates on the phase modulated beam 217 to produce an amplitude modulated beam 281 (which will be incident on surface 237 of sample 235). In this example, the polarizer 280 has a polarization of −45. However, the polarizer 280 may also have other polarizations, such as +45. A discussion of using EOMs to produce amplitude modulation is given in Robert F. Enscoe and Richard J. Kocka, "Systems and Applications Demands for Wider-Band Beam Modulation Challenge System Designers", copyright 1981-2005 by Conoptics Inc.

The one or more characteristics 285 for optical stress generation and detection may include, e.g., thickness of thin films on the sample, thermal, elastic, and optical properties of thin films, stress in thin films; and characterization of the properties of interfaces, including the presence of roughness and defects. Additional characteristics 285 can include pattern size for patterns on the sample 235.

FIG. 5 is an exemplary graph of retardation applied by the EOM in FIG. 4 and resultant polarization occurring in the phase modulated beam 217. In this example, the retardation applied by the EOM 215 is shown as a sinusoidal signal 510 and indicates a retardation in polarization from "zero" to half-wave ($\lambda/2$) retardation (e.g., the EOM 215 acts as a half-wave plate). The retardation portion of FIG. 5 shows a sinusoidal control signal 412 (e.g., as a voltage) that is applied to the EOM 215 to create the corresponding retardation waveform. The sinusoidal control signal 412 is sinusoidally varied between $$V_{\lambda/2} \text{ and } -V_{\lambda/2}.$$

When the retardation is zero, the polarization is +45 degrees (e.g., the polarization of the polarized beam 211). When the retardation is $\lambda/2$, the polarization is −45 degrees. When the retardation is $-\lambda/2$, the polarization is also −45 degrees. Thus, the polarization of the phase modulated beam 217 remains primarily linear and circular polarization (or elliptical polarization) is not used. Beam 281, which occurs after the polarizer 280, is intensity modulated as and varies between $I_H$ and $I_L$.

The combination of varying the one or more control signals 412, which cause the EOM 215 to vacillate between linear polarizations (see FIG. 5), and use of the polarizer 280 therefore causes intensity modulation of the beam 281, which will be incident on the surface 237 of the sample 235 (e.g., after being redirected by the mirror 220 and passing through the lens 230).

It is noted that sinusoidal signal 510 is merely one example of a retardation modulation signal. Sawtooth signal 520 may also be used, as could a number of other signals.

Figure 6:
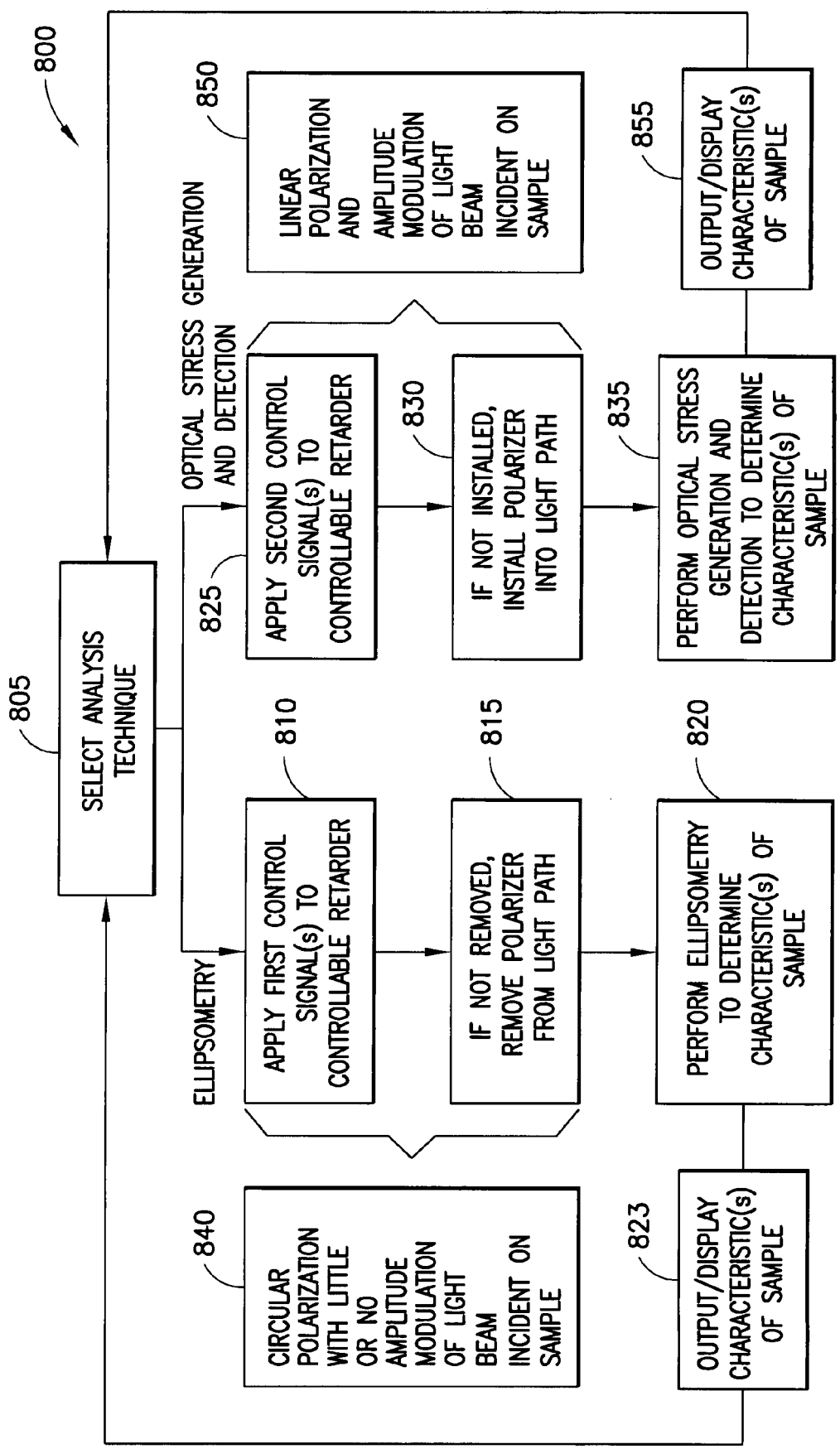
FIG. 6 is a method for performing combination ellipsometry and optical stress generation and detection.

Turning now to FIG. 6, a method 800 is shown for performing both ellipsometry and optical stress generation and detection. Method 800 begins in block 805, when an analysis technique is selected. Typically, the selection would be performed by a user, although it is possible that selection could be performed through other techniques. In particular, for automated techniques, when measurements are to be performed on a sample, ellipsometry could always be selected and then optical stress generation and detection would be selected (for instance).

In response to ellipsometry being chosen (block 805), one or more first control signals are applied to a controllable retarder, such as an electro-optic modulator, an LCD based phase modulator, or possibly a photoelastic modulator, in block 810. The first control signal(s) is defined to at least partially (e.g., periodically) bring about circular polarization of the light beam incident on the sample, as shown in FIG. 3. It is noted that the polarization of the incident light beam varies with time and circular polarization occurs at certain determinable time periods. In one exemplary embodiment, the first control signals include a bias voltage to bias the voltage to the electro-optic modulator such that the controllable retarder acts as a periodically controlled quarter-wave plate. The first control signals also include a modulation signal, such as a sinusoidal or linear signal. In block 815, the polarizer (e.g., polarizer 215 of FIG. 2 or polarizer 280 of FIG. 5) is removed from the light path, if the polarizer has not already been removed. Thus, blocks 810 and 815 allow the controllable retarder and system to modify the incident light beam (block 840) to create substantially circular polarization periodically. In block 820, ellipsometry is performed using the modified light beam in order to determine one or more characteristics of the sample. The one or more characteristics of the sample may be output and/or displayed in block 823.

In response to optical stress generation and detection being chosen (block 805), one or more second control signals are applied to the controllable retarder, such as an electro-optic modulator or possibly a photoelastic modulator; in block 825. The second control signals are defined to at least partially cause a time-varying linear polarization of the light beam. The linear polarization could vary between −45 and 45 degrees, for instance. In one exemplary embodiment, second control signals include a bias voltage to bias the voltage to the controllable retarder such that the electro-optic modulator acts as a half-wave plate. The second control signals also include a modulation signal, such as a sinusoidal signal. In block 830, a polarizer (e.g., polarizer 280 of FIG. 4) is installed in the light path after the controllable retarder but prior to the sample, if the polarizer has not already been installed. Thus, blocks 825 and 830 allow the controllable retarder and system to modify the incident light beam by performing time-varying linear polarization, which in conjunction with a polarizer causes amplitude modulation of the light beam incident on the sample (block 850). In block 835, optical stress generation and detection is performed using the modified light beam in order to determine one or more characteristics of the sample. In block 855, the one or more characteristics may be output and/or displayed.

Now that the operation has been described of a system able to perform both ellipsometry and optical stress generation and detection, additional systems are now described.

Figure 7:
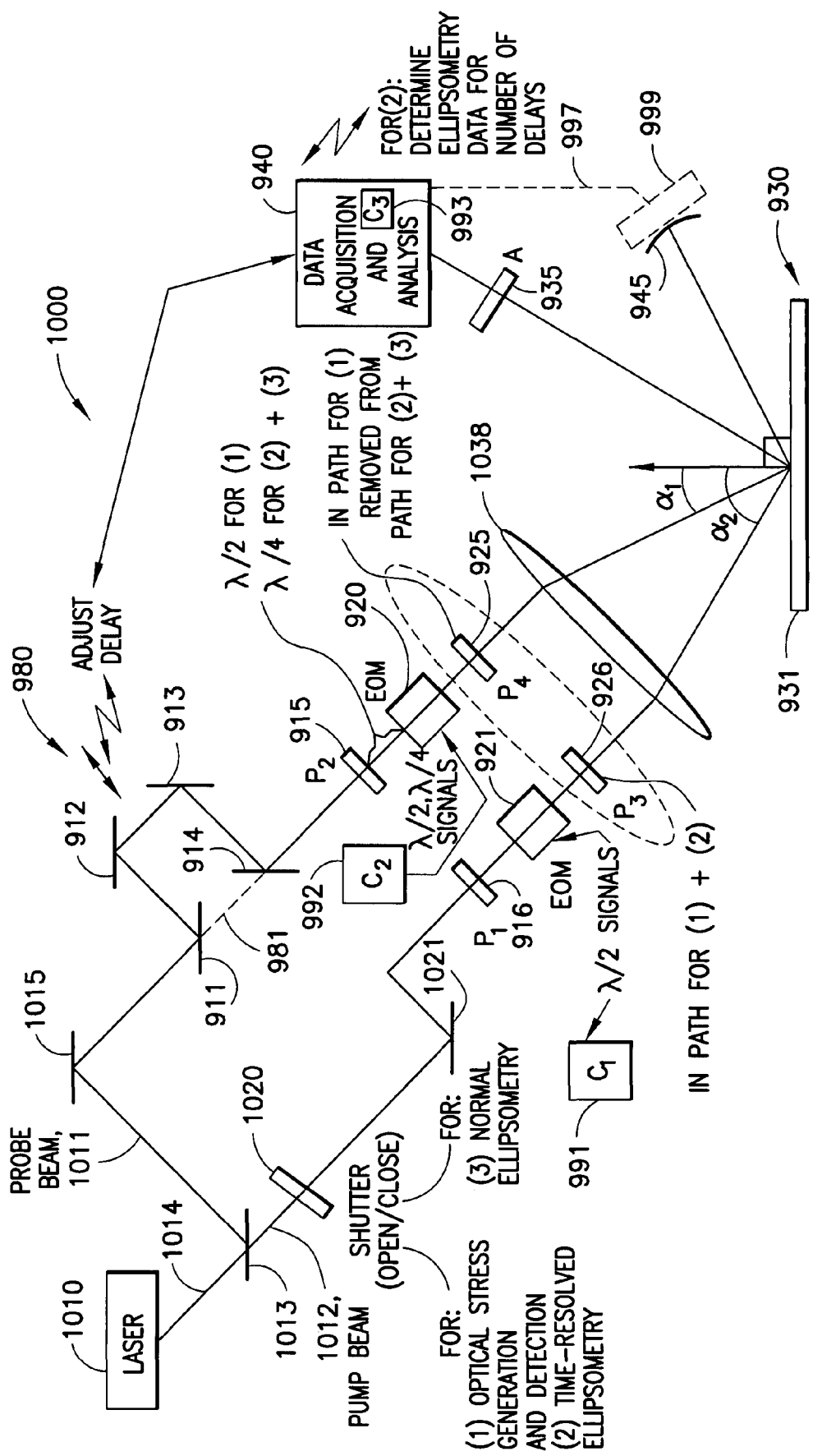
FIG. 7 is a block diagram of an exemplary system for performing both ellipsometry and optical stress generation and detection with separate pump and probe beams.

Referring to FIG. 7, an exemplary system 1000 is shown for performing both ellipsometry and optical stress generation and detection with separate pump and probe beams. System 1000 includes a laser 1010 and mirrors 911,912, 913, and 914. System 1000 includes a splitter 1013 that creates both pump beam 1012 and probe beam 1011 from one light beam 1014 from laser 1010. The mirrors 912 and 913 are movable to produce a time delay between the pump beam 907 and probe beam 906. The mirrors 911-914 form a time delay mechanism 980. The mirrors 911-914 are merely one example of a time delay mechanism 980, and any mechanism for adjusting delay between the probe beam 1011 and the pump beam 1012 may be used. In this example, delay is adjusted by using a controller $C_3$ 993 in the data acquisition and analysis module 940, and the controller controls positioning of the time delay mechanism 980. The system 1000 also includes polarizers $P_2$ 915, $P_1$ 916, EOMs 920, 921, two movable polarizers $P_4$ 925, $P_3$ 926, an analyzer 935, a data acquisition and analysis module 940 (which includes in this example a detector that is not shown), and a photon motel 945. The pump beam 1012 and probe beam 1011 are directed onto the surface 931 of the sample 930 at particular angles of incidence, $\alpha_1$ and $\alpha_2$. It is noted that the photon motel 945 could be replaced by a detector 999, which would be coupled to the data acquisition and analysis module 940 and would provide a second measurement at a second angle of incidence (i.e., $\alpha_2$ in addition to $\alpha_1$).

The EOMs 920, 921 would have appropriate control signals depending on into which configuration (e.g., ellipsometry or optical stress generation and detection) the system 1000 is configured. In an exemplary embodiment, the EOM 921 is supplied (e.g., by controller $C_1$ 991) with only signals to produce periodic λ/2 retardation, while the EOM 920 (e.g., by controller $C_2$ 992) is supplied with either signals to produce periodic λ/2 retardation (for a configuration where optical stress generation and detection is performed) or signals to produce periodic λ/4 retardation (for a configuration where ellipsometry is performed). The polarizer $P_4$ is removed from the path of the probe beam 1011 when "normal" ellipsometry (another type of ellipsometry is discussed below) is performed. The shutter 1020 is used to block the pump beam 1012 when normal ellipsometry is performed. It is noted that the controllers 991, 992 could be combined and could be programmed, e.g., electronically or manually.

One or both of the movable polarizers 925, 926 would be moved into position (i.e., into the path of the pump beam 907 and probe beam 906) during a configuration of the system 1000 to perform optical stress generation and detection and one of the movable polarizers 925, 926 would be removed when the system 1000 is placed into a configuration to perform ellipsometry. Note that in this example, the probe beam 906 may also bypass the time delay mechanism 980 by following path 981. Path 981 may be created by removing mirrors 911, 914 or by moving the mirrors 911, 914 so that the mirrors do not impede the probe beam 1011. A lens 1038 is used to focus the pump beam 1012 and probe beam 1011 onto the surface 931 of the sample 930.

As described above, the shutter 1020 is used to turn off the pump beam 1012 during "normal" single-beam ellipsometry. The shutter 1020 would be open during optical stress generation and detection and also for time-resolved ellipsometry. Time resolved ellipsometry is described in Applied Physics Letters, vol. 63, page 1507 (1993), and is briefly described herein. In "normal" ellipsometry, only a single light beam is used, as described above. For time-resolved ellipsometry, the EOM 920 is set up as a quarter-wave plate (λ/4 signals are applied to the EOM 920), the polarizer $P_4$ is removed from the path of the probe beam 1011, the EOM 921 is set up as a half-wave plate (λ/2 signals are applied to the EOM 921), and the polarizer $P_3$ is placed in (e.g., not removed from) the path of the probe beam 1011.

In time-resolved ellipsometry, two beams are used just as in optical stress generation and detection: the pump beam 1012 and probe beam 1011. However, reflection ellipsometry data (e.g., Δ and Ψ) are examined as a function of time delay between the pump beam and probe beam. This can be thought of in a broad sense as capturing a motion picture of what happens to the probe beam as a function of the pump beam. For instance, the time delay mechanism 980 could be adjusted so that the probe beam 1011 arrives at the surface 931 one picosecond prior to arrival of the pump beam 1012. When the probe beam 1011 arrives at the surface 931 prior to the arrival of the pump beam 1012, the delay is considered to be negative. The time delay mechanism 980 would be adjusted so that the delay is modified, for instance, from some negative delay to some positive delay. Such adjustment in delays generally includes certain intervals of delay. At each delay, the reflection ellipsometry data is gathered. It is noted that if normal ellipsometry will not be performed and instead time-resolved ellipsometry will be performed in addition to optical stress generation and detection, then the shutter 1020 will typically not be used.

Figure 8:
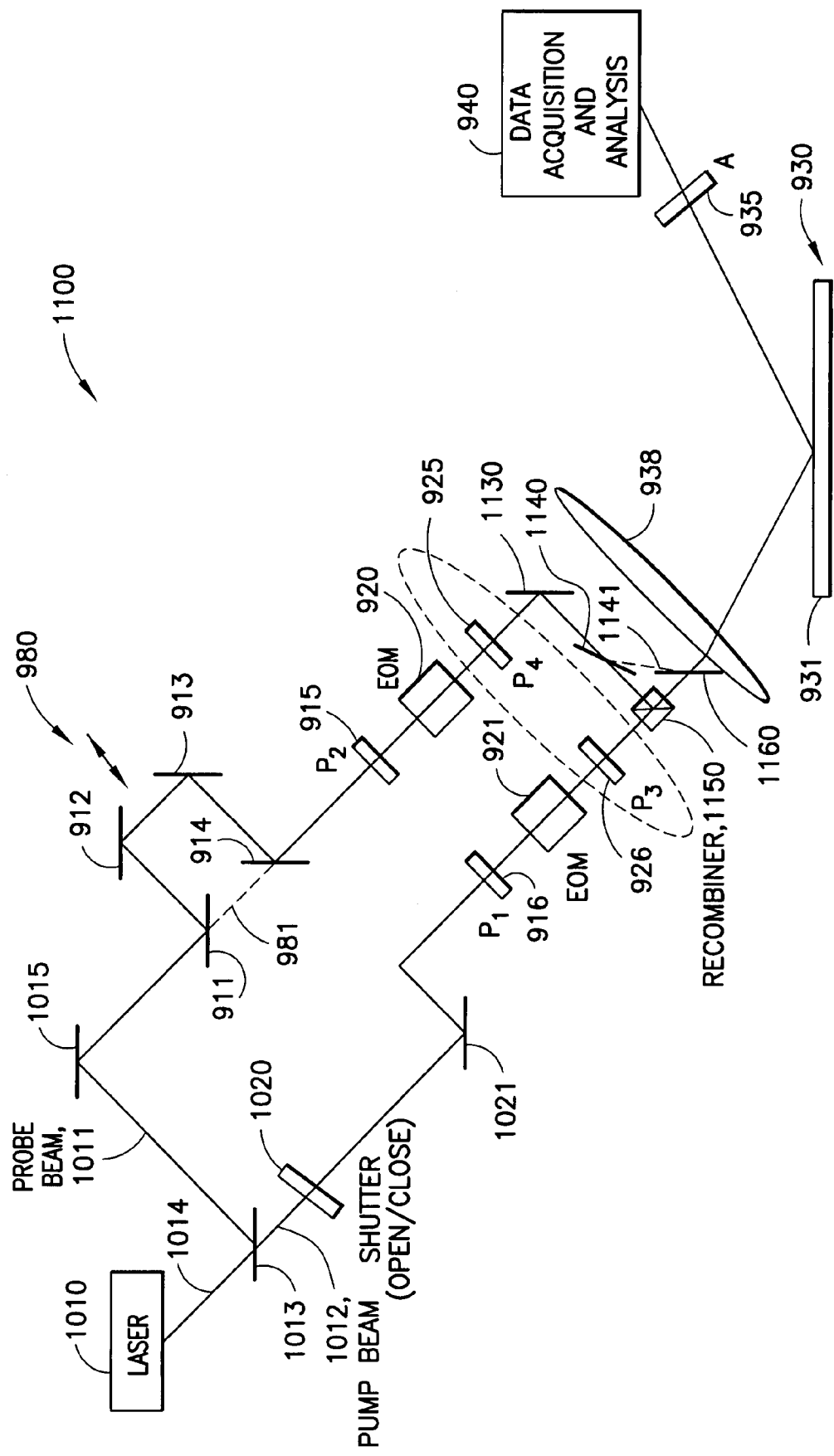
FIG. 8 is a block diagram of a system for performing both ellipsometry and optical stress generation and detection with combined pump and probe beams.

Turning now to FIG. 8, a system 1100 is shown for performing both ellipsometry and optical stress generation and detection with combined (e.g., collinear) pump and probe beams. System 1100 includes mirrors 1130, 1140, and 1160, and a recombiner 1150. In a configuration when "normal" single-beam ellipsometry is being performed, the mirror 1130 and recombiner 1150 would be used.

Figures 9, 10:
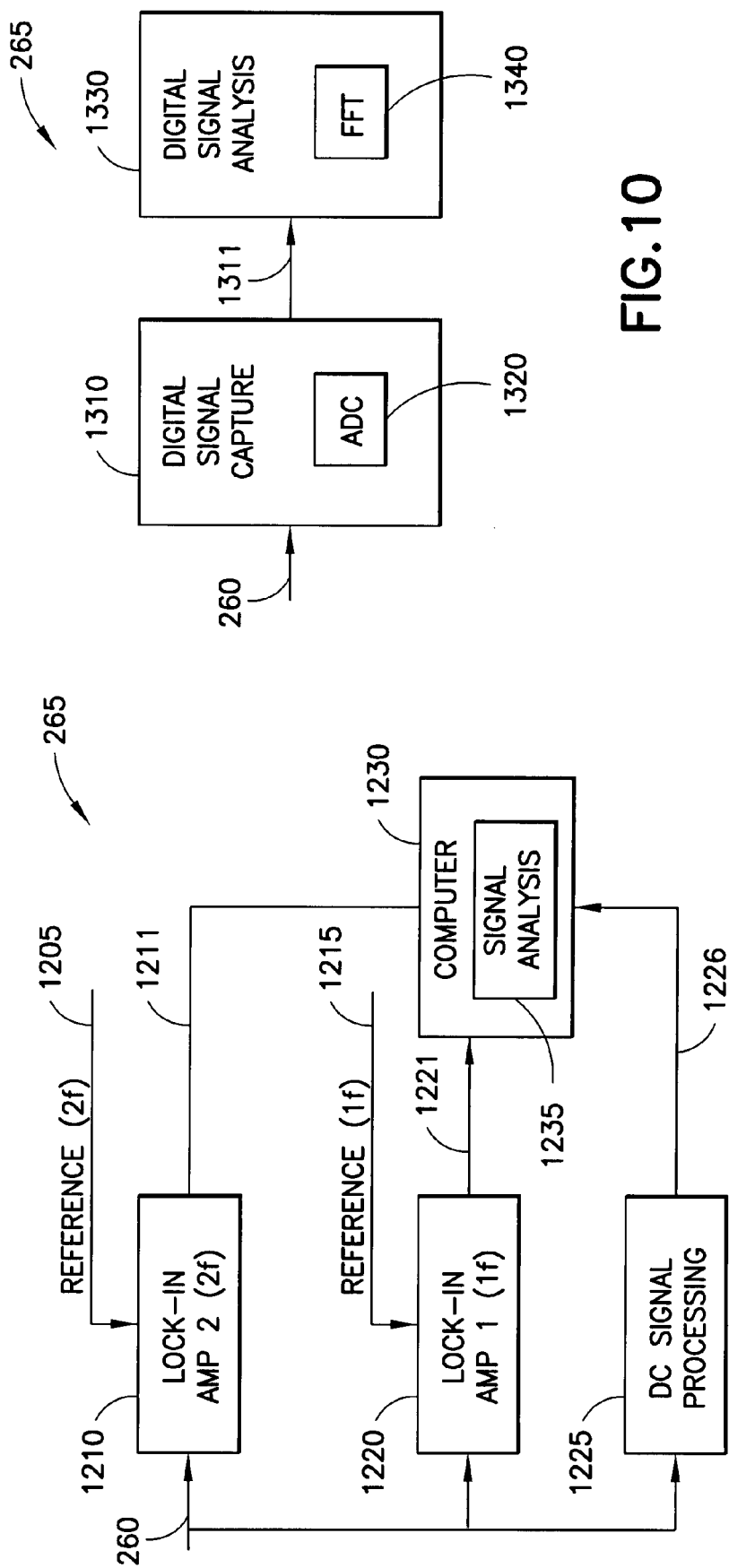
FIG. 9 is a block diagram of an exemplary data acquisition module.
FIG. 10 is a block diagram of another exemplary data acquisition module.

Turning now to FIG. 9, a block diagram is shown of an exemplary data analysis module 265, where the data analysis module 265 does not have a corresponding control function. The data analysis module 265 includes two lock-in amplifiers

1210, 1220, a DC signal processing module 1225, and a computer 1230. The lock-in amplifier 1220 uses a reference clock 1215, and is configured to lock onto signals at f, the modulation frequency. The lock-in amplifier 1230 uses a reference clock 1205 and is configured to lock onto signals at 2f, twice the modulation frequency. The computer 1230 includes a signal analysis program 1235 configured to determine properties of a sample based on the outputs 1211, 1221, and 1226.

Referring to FIG. 10, a block diagram is shown of another exemplary data acquisition module 265, where the data analysis module 265 does not have a corresponding control function. This exemplary data acquisition module 265 includes a digital signal capture module 1310 that includes an analog-to-digital converter (ADC) 1320, which creates digital data 1311. The data acquisition module 265 also includes a digital signal analysis module 1330, which includes a fast Fourier transform (FFT) module 1340. It is noted that the digital signal analysis module 1330 could be a computer or include a digital oscilloscope.

The data acquisition modules 265 shown in FIGS. 9 and 10 are merely exemplary and may include control function(s) to control a portion or all of a system.

The previous embodiments had a light beam be directed toward the surface of a sample at a single incident angle. However, the present invention may be used with multiple incident angles. FIGS. 11 (including FIGS. 11A-11C) and 12 (including FIGS. 12A-12C) include examples for creating multiple incident angles.

Turning now to FIG. 11A, a diagram is shown of a system 1600 used to direct light beams 1605a and 1605b to a sample 1630. The system 1600 includes a number of mirrors 1610, 1615, 1640, and 1645 and two lenses 1620 and 1635. The system 1600 could be used in the systems shown in FIGS. 7 and 8, and light beams 1605a and 1605b represent pump and probe beams in those systems. The light beams 1605a and 1605b are directed to the surface 1631 of the sample 1630 at angles of incidence, $\alpha_1$ and $\alpha_2$, respectively. FIGS. 11B and 11C show how a path of a single one of the light beams 1605a, 1605b can be deflected so that the light beam will create multiple angles of incidence relative to the surface 1631 of the sample 1630. FIG. 11B is a diagram of another system for providing a number of angles of incidence of a light beam. The acousto-optic deflector 1655 deflects the light beam 1605a to cause one of the light beams 1608 (e.g., along an in initial path) and 1609 (along a deflected path). In other words, the light beam 1608 occurs when the acousto-optic deflector (AOD) causes no deflection, and light beam 1609 occurs when the AOD causes a small amount of deflection. The angles of incidence, $\theta_1$ and $\theta_2$ are shown. FIG. 11C is another diagram of a system for providing a number of angles of incidence of a light beam. In this example, a piezo-motor (PM) 1660 moves the mirror 1615 to create two angles of incidence, $\theta_1$ and $\theta_2$. Again, the angle of incidence $\theta_1$ would be created with the piezo-motor at one location and the angle of incidence $\theta_2$ would be created with the piezo-motor at a second location.

Other techniques may also be used to create simultaneous multiple angles of incidence. See, e.g., the measurement techniques described in U.S. Pat. No. 5,166,752. In this patent, a lens is used to create a plurality of multiple angles of incidence and a detector is used to resolve at least some of the different angles of incidence.

Figure 12A:
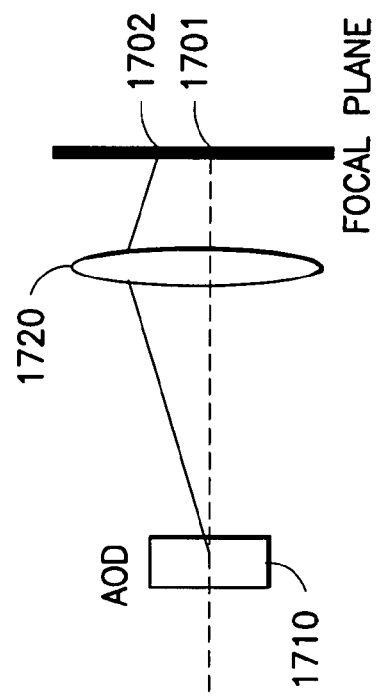
FIG. 12A is a diagram of a portion of an acousto-optic deflector (AOD) system to show that AOD may not focus in a "correct" location.
Figure 12B:
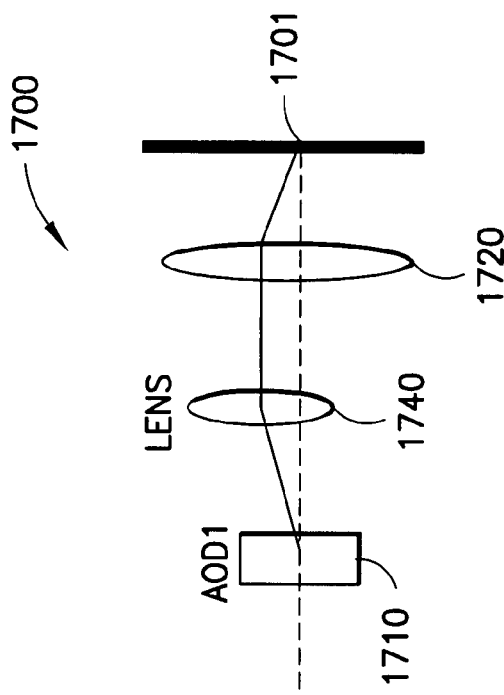
FIGS. 12B and 12C are diagrams of portions of an AOD system to correct for misalignment of focusing.
Figure 12C:
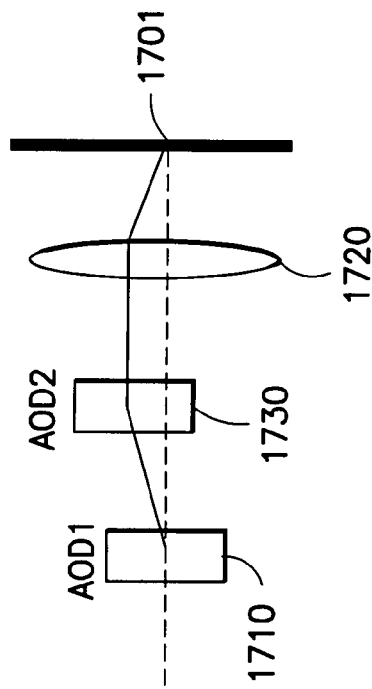

Turning now to FIG. 12A, a diagram is shown of a portion of an AOD system to show that AOD may not focus in a "correct" location. It can be seen that using the AOD 1710 and lens 1720 causes a deviation from the correct focal location 1701 to an incorrect focal location 1702. This misalignment can be corrected, however. FIGS. 12B and 12C are diagrams of portions of an AOD system to correct for misalignment of focusing. In FIG. 122B, the misalignment is corrected by using a second AOD 1730. In FIG. 12C, the misalignment is corrected by using a second lens 1710.

Figure 13:
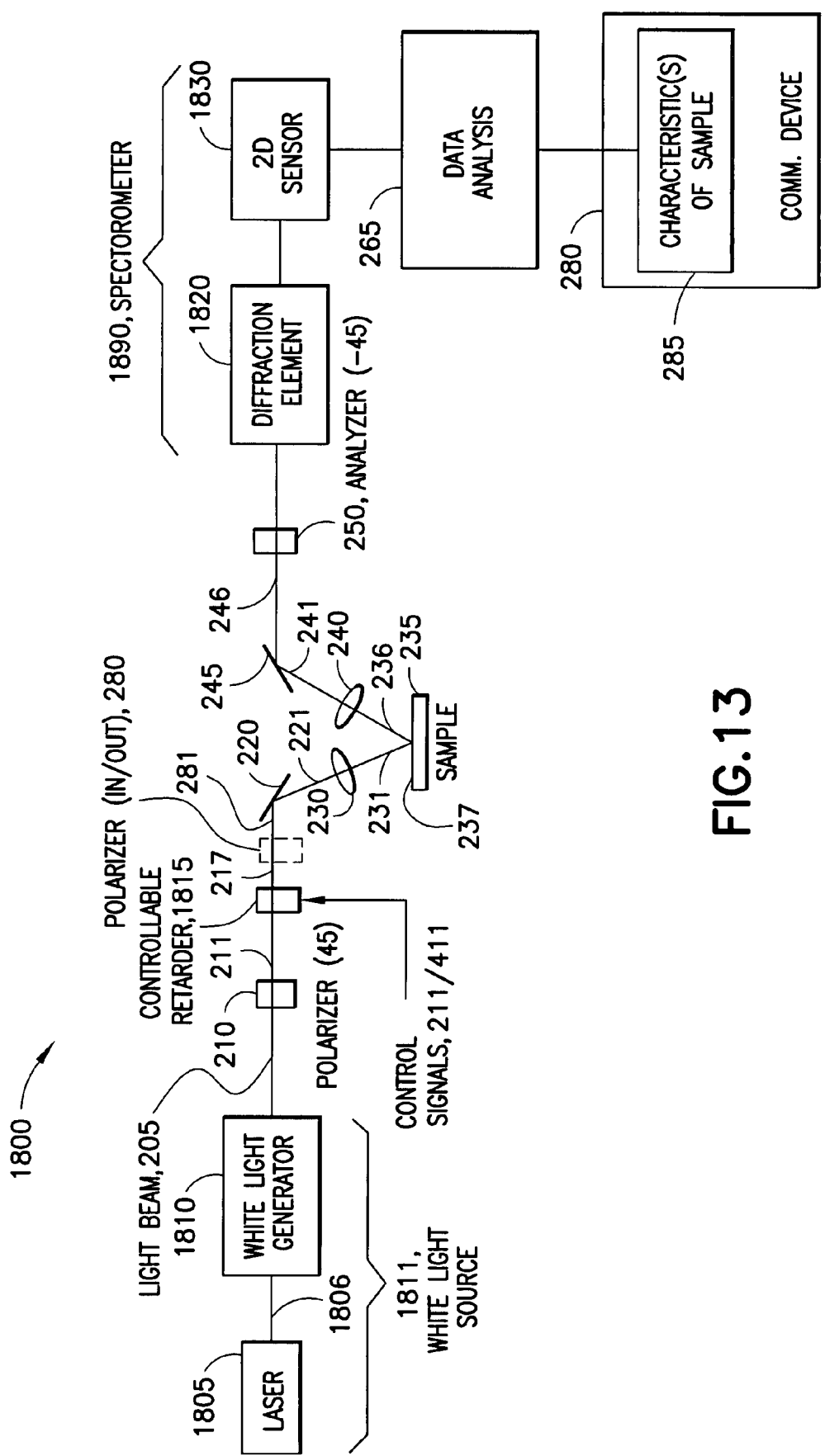
FIG. 13 is an example of the system of FIGS. 2 and 4 modified to perform multi-frequency measurements for one or both of ellipsometry or optical stress generation and detection.

It should be noted that multiple frequency measurements may be performed (such as by using spectroscopic ellipsometers). Many different types of white light sources may be used. In one embodiment of system 1800, shown in FIG. 13, 800 nm pulses of light 1806 having a bandwidth of about 12 nm, created by laser 1805, can be passed through a white light generator 1810 positioned immediately before polarizer 210 in FIG. 2 to generate a supercontinuum which provides a light beam 205 having multiple wavelengths. Generation of a supercontinuum is described in, e.g., Phys. Rev. Lett. Vol. 24, page 592 (1970). Thus, white light source 1811 includes in this non-limiting example a laser 1805 and a white light generator 1810. The controllable retarder 1815 is configured by suitable control signals 211/411, and the polarizer 280 is added into the path of the light beam (for optical stress generation and detection) or taken out of the path of the light beam (for ellipsometry). When used in conjunction with a suitable diffraction element 1820 and a suitable two-dimensional (2D) sensor 1830, spectroscopic ellipsometry measurements may also be obtained. It should also be noted that multiple frequency measurements may be performed with the help of the supercontinuum and a spectrometer 1890, which renders a device with an additional functionality of spectroscopic ellipsometry measurements.

It is noted that aspects of the invention may be implemented as a computer-readable medium having a program of computer-readable instructions tangibly embodied thereon, the instructions executable by a processing unit to perform operations described herein. The computer-readable medium may, e.g., reside in a memory of a processing unit or reside on a Compact Disk (CD), Digital Versatile Disk (DVD), memory stick, or other long-term storage.

The foregoing description has provided by way of exemplary and non-limiting examples a full and informative description of the best techniques presently contemplated by the inventors for carrying out embodiments of the invention. However, various modifications and adaptations may become apparent to those skilled in the relevant arts in view of the foregoing description, when read in conjunction with the accompanying drawings and the appended claims. All such and similar modifications of the teachings of this invention will still fall within the scope of this invention.

Furthermore, some of the features of exemplary embodiments of this invention could be used to advantage without the corresponding use of other features. As such, the foregoing description should be considered as merely illustrative of the principles of embodiments of the present invention, and not in limitation thereof. In particular, the dependent claims herein can be combined, e.g., as multiple-dependent claims unless the dependent claims themselves prevent such a combination. For example, the first and second characteristics of the sample could be output and/or displayed to a user, regardless of whether the controllable retarder is a photoelastic modulator (PEM), an LCD (liquid crystal display) based phase modulator, or an electro-optic modulator (EOM).

What is claimed is:

1. A method, comprising:
   selecting at least one of performing ellipsometry and performing optical stress generation and detection;
   in response to selecting performing ellipsometry, applying at least one first control signal to a controllable retarder that modifies at least a polarization of a light beam directed to a surface of a sample to generate a first modified light beam, and performing ellipsometry using a first reflected version of the first modified light beam reflected from the sample in order to determine at least one first characteristic of the sample; and in response to selecting performing optical stress generation and detection, applying at least one second control signal to the controllable retarder to generate a second modified light beam, and performing optical stress generation and detection using a second reflected version of the second modified light beam in order to determine at least one second characteristic of the sample.

2. The method of claim 1, wherein the controllable retarder comprises one of an electro-optic modulator (EOM), a photoelastic modulator (PEM) and an LCD (liquid crystal display) based phase modulator.

3. The method of claim 1, further comprising outputting at least one of the at least one first characteristic and the at least one second characteristic of the sample.

4. The method of claim 3, further comprising displaying at least one of the output the at least one first characteristic and the at least one second characteristic.

5. The method of claim 1, wherein:
the at least one first control signal is configured to cause the controllable retarder to create a periodic elliptical polarization of the light beam; and
the at least one second control signal is configured to cause the controllable retarder to create a periodic linear polarization of the light beam.

6. The method of claim 5, wherein the at least one first control signal and the at least one second control signal is one of a sinusoidal signal or a sawtooth signal.

7. The method of claim 5, wherein the at least one first control signal is configured to cause the controllable retarder to create periodic circular polarization of the light beam.

8. The method of claim 5, further comprising, in response to performing optical stress generation and detection, placing a polarizer into a path of the second modified light beam, wherein the polarizer and the at least one control signal are defined to cause at least an amplitude modulation of a light beam exiting the polarizer.

9. The method of claim 8, wherein the light beam is a probe beam when the light beam is used for optical stress generation and detection and
wherein the light beam is a pump beam when the light beam is used for optical stress generation and detection.

10. The method of claim 1, further comprising one of:
directing the first modified light beam to the surface of the sample so that the first modified light beam has a first angle of incidence with respect to the surface of the sample and directing the first modified light beam to the surface of the sample so that the first modified light beam has a second angle of incidence with respect to the surface of the sample, wherein ellipsometry is performed using information from the first reflected version of the first modified light beam corresponding to the first and second angles of incidence; and
directing the second modified light beam to the surface of the sample so that the second modified light beam has a first angle of incidence with respect to the surface of the sample and directing the second modified light beam to the surface of the sample so that the second modified light beam has a second angle of incidence with respect to the surface of the sample, wherein optical stress generation and detection is performed using information from the second reflected version of the second modified light beam corresponding to the first and second angles of incidence.

11. The method of claim 1, further comprising:
generating the light beam, where the light beam comprises a first plurality of wavelengths and
one of:
diffracting the first reflected version of the modified light beam to separate the first reflected version into a second plurality of wavelengths, wherein ellipsometry is performed using the second plurality of wavelengths; and
diffracting the second reflected version of the second modified light beam to separate the second reflected version into a third plurality of wavelengths, wherein optical stress generation and detection is performed using the third plurality of wavelengths.

12. An apparatus having at least a first configuration used to perform ellipsometry and a second configuration used to perform optical stress generation and detection, comprising:
an optical source configured to generate a pump beam and a probe beam, where each of the beams is directed to a surface of a sample;
a controllable retarder placed in a path of a selected one of the pump beam or the probe beam, the controllable retarder configured to modify at least a polarization of the selected beam in response to a control signal;
a controller configured to provide at least one control signal to the controllable retarder, wherein the controller is configured in the first configuration to cause at least one first control signal to be applied to the controllable retarder, the controller configured in the second configuration to cause at least one second control signal to be applied to the controllable retarder, wherein the at least one first control signal and the at least one second control signal are configured to cause different polarizations of the selected beam;
a detector configured to receive a version of the selected beam reflected from the surface of the sample and to output data corresponding to the reflected version; and
a data analysis module coupled to the detector and configured in the first configuration to perform data analysis using the output data in order to determine at least one first characteristic of the sample, and further configured in the second configuration to perform data analysis using the output data in order to determine at least one second characteristic of the sample.

13. The apparatus of claim 12, wherein the controllable retarder comprises one of an electro-optic modulator (EOM), a photoelastic modulator (PEM) and an LCD (liquid crystal display) based phase modulator.

14. The apparatus of claim 12, further comprising a communication device configured to display at least one of the at least one first characteristic and the at least one second characteristic.

15. The apparatus of claim 12, wherein:
the at least one first control signal is configured to cause the controllable retarder to create periodic elliptical polarization of the selected beam; and
the at least one second control signal is configured to cause the controllable retarder to create periodic linear polarization of the selected beam.

16. The apparatus of claim 15, wherein the at least one first control signal is defined to create periodic circular polarization of the selected beam.

17. The apparatus of claim 15, further comprising a movable polarizer configured to be placed, in the second configuration, into a path of the modified selected beam and configured to be removed, in the first configuration, from the path of the modified selected beam, wherein the movable polarizer and the at least one second control signal are configured to cause at least an amplitude modulation of the modified selected beam exiting the movable polarizer.

18. The apparatus of claim 12, wherein the selected beam is the probe beam, the controllable retarder is a first controllable retarder placed in a path of the probe beam, the controller is a first controller, and wherein the apparatus further comprises:
 a shutter placed in a path of the pump beam and configured in the first configuration to block the pump beam, the shutter configured in the second configuration to pass the pump beam;
 a second controllable retarder placed in a path of the pump beam, the second controllable retarder configured to modify at least the polarization of the pump beam;
 a second controller coupled to the second controllable retarder and configured to provide at least one control signal to the second controllable retarder, wherein the second controller is configured in the second configuration to cause at least one third control signal to be applied to the controllable retarder.

19. The apparatus of claim 18, further comprising a movable polarizer configured to be placed, in the second configuration, into a path of the modified probe beam and configured to be removed, in the first configuration, from the path of the probe beam, wherein the movable polarizer and the at least one second control signal are defined to cause at least amplitude modulation of the probe beam exiting the movable polarizer, wherein the apparatus further comprises another polarizer placed into a path of the modified pump beam, and wherein the another polarizer and the at least one third control signal are configured to cause at least an amplitude modulation of the probe beam exiting the movable polarizer.

20. The apparatus of claim 19, further comprising a time delay mechanism configured to be placed in the path of the probe beam and configured to adjust a delay of the probe beam relative to the pump beam, and wherein the data analysis module is further configured to determine ellipsometry data for a plurality of delays.

21. The apparatus of claim 12, further comprising an acousto-optic deflector, at least one mirror, and a lens configured to be positioned in the path of the selected beam, wherein the acousto-optic deflector is configured to displace the selected light beam from an initial path to a displaced path so that the selected beam has a first angle of incidence with respect to the surface of the sample in the initial path and the selected beam has a second angle of incidence with respect to the surface of the sample in the displaced path.

22. The apparatus of claim 12, further comprising at least one mirror, a piezo-motor coupled to a selected one of the at least one mirrors, and a lens positioned in the path of the selected beam, wherein the piezo-motor is configured to move the selected mirror to displace the selected light beam from an initial path to a displaced path so that the selected beam has a first angle of incidence with respect to the surface of the sample in the initial path and the selected beam has a second angle of incidence with respect to the surface of the sample in the displaced path.

23. The apparatus of claim 12, where the optical source is a white light source and where the selected beam comprises a first plurality of wavelengths; and further comprising:
 a diffraction element placed in a path of the reflected version of the selected beam, wherein the diffraction element is configured to diffract the reflected version of the selected beam to separate the reflected version into a second plurality of wavelengths and to direct the second plurality of wavelengths onto the detector,
 wherein the detector comprises a two-dimensional sensor configured to resolve information corresponding to the second plurality of wavelengths.

24. A non-transitory computer-readable medium having a program of computer-readable instructions tangibly embodied thereon, the instructions executable by a processing unit to perform operations comprising:
 selecting one of performing ellipsometry or performing optical stress generation and detection;
 in response to selecting performing ellipsometry, applying at least one first control signal configured to instruct to a controllable retarder to modify at least a polarization of a light beam directed to a surface of a sample to generate a first modified light beam, and performing ellipsometry using a first reflected version of the first modified light beam reflected from the sample in order to determine at least one first characteristic of the sample; and
 in response to selecting performing optical stress generation and detection, applying at least one second control signal configured to instruct to the controllable retarder to generate a second modified light beam, and performing optical stress generation and detection using a second reflected version of the second modified light beam in order to determine at least one second characteristic of the sample.

\* \* \* \* \*